United States Patent [19]
Kuwada et al.

[11] 3,947,417
[45] Mar. 30, 1976

[54] TRIAZOLOBENZODIAZEPINE DERIVATIVES

[75] Inventors: Yutaka Kuwada, Hyogo; Hiroyuki Tawada, Osaka; Kanji Meguro, Hyogo, all of Japan

[73] Assignee: Takeda Chemical Industries, Ltd., Japan

[22] Filed: Feb. 19, 1974

[21] Appl. No.: 443,528

[30] Foreign Application Priority Data
Feb. 19, 1973 Japan................................ 48-19930

[52] U.S. Cl....... 260/244 R; 260/193; 260/247.1 E; 260/243 R; 260/247.2 A; 260/256.4 F; 260/268 PC; 260/293.57; 260/293.58; 260/293.59; 260/306.7 R; 260/307 FA; 260/308 R; 424/248; 424/272

[51] Int. Cl.² C07D 487/14; C07D 498/14; C07D 513/14

[58] Field of Search...... 260/307 FA, 244 R, 243 R, 260/256.4 F, 268 PC, 306.7 R, 247.2

[56] References Cited
UNITED STATES PATENTS

| 3,701,782 | 10/1972 | Hester............................ 260/308 R |
| 3,755,300 | 8/1973 | Tachikawa et al........... 260/239.3 T |

OTHER PUBLICATIONS
Meguaro et al., Chem. Abstracts, Vol. 77, Abstract No. 88557k, (1972).
Gagneux et al., Chem. Abstracts, Vol. 79, Abstract No. 126535c, (1973).

Primary Examiner—Alton D. Rollins
Attorney, Agent, or Firm—Wenderoth, Lind & Ponack

[57] ABSTRACT

Compounds of the formula:

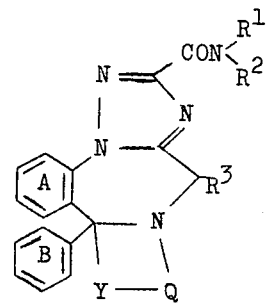

wherein $R^1$ and $R^2$ are the same or different and each stands for hydrogen atom or alkyl group which may be substituted by hydroxy or/and alkoxy group; $R^1$ and $R^2$ may, taken together with the adjacent nitrogen atom, form a heterocyclic ring; $R^3$ stands for hydrogen atom or lower alkyl group; Q stands for ethylene or trimethylene group which may be substituted by lower alkyl group; Y stands for —O—, —S— or —NH—; and rings A and B are unsubstituted or substituted by halogen atom, nitro, alkyl, trifluoromethyl or/and alkoxy group, and pharmaceutically acceptable salts thereof, are useful as tranquilizers, muscle relaxants, sedatives, anticonvulsants, sleep inducers, etc.

13 Claims, No Drawings

TRIAZOLOBENZODIAZEPINE DERIVATIVES

The present invention relates to novel benzodiazepine derivatives of the following general formula (I):

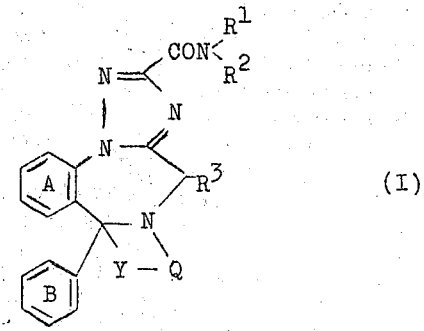

(wherein $R^1$ and $R^2$ are the same or different and each stands for hydrogen atom or alkyl group which may be substituted by hydroxy or/and alkoxy group. $R^1$ and $R^2$ may, taken together with the adjacent nitrogen atom, form a heterocyclic ring; $R^3$ stands for hydrogen atom or lower alkyl group; Q stands for ethylene or trimethylene group which may be substituted by lower alkyl group; Y stands for —O—, —S— or —NH—; and rings A and B are unsubstituted or substituted by halogen atom, nitro, alkyl, trifluoromethylene or/and alkoxy group) and their pharmaceutically acceptable salts.

The present inventors have made extensive study about a series of benzodiazepine derivatives and succeeded in synthesizing the novel derivatives of the above formula (I), and have found out that the above benzodiazepine derivatives have an effective tranquilizing effect, etc.

The present invention has been accomplished on the basis of this finding.

The principal object of this invention is to provide novel benzodiazepine derivatives useful as a tranquilizer, etc. Another object of this invention is to provide a method for the production of these novel compounds. Further objects will become apparent from the description of this specification as well as of the claims.

The following is a detailed explanation of this invention.

Referring to the above general formula (I), the alkyl groups denoted by $R^1$ and $R^2$ are preferably straight-chain, branched or cyclic lower alkyl groups of 1 to 6 carbon atoms, such as methyl, ethyl, propyl, isopropyl, butyl, pentyl, cyclopentyl, hexyl, cyclohexyl, etc. When the alkyl $R^1$ or $R^2$ is substituted by hydroxy or alkoxy, the alkyl group may be substituted in optional positions by an optional number of hydroxy group(s) or/and lower alkoxy group(s) of about 1 to 4 carbon atoms (for example, methoxy, ethoxy, propoxy, isoproxy, butoxy, etc.). Such substituted alkyls are exemplified by 2-hydroxyethyl, 2-hydroxypropyl, 3-hydroxypropyl, 2-methoxyethyl, 2-ethoxyethyl, 2,2-dimethoxyethyl, 2,2-diethoxyethyl, 3-methoxypropyl, 3-ethoxypropyl, 2-methoxypropyl, 2-ethoxypropyl, etc. The heterocyclic group which may be formed by $R^1$ and $R^2$ as taken together with the adjacent nitrogen atom is preferably a five- to seven-membered ring including, as one hetero-atom or hetero-atoms, 1 to 2 nitrogen, oxygen, sulfur atom(s). The heterocyclic ring may be substituted in optional positions by alkyl, hydroxyalkyl or/and alkoxyalkyl groups same with those mentioned for $R^1$ and $R^2$. Examples of such heterocyclic ring are pyrrolidine, piperidine, homopiperazine, homopiperidine, morpholine, piperazine, N-mono-substituted piperazine (e.g. N-methyl-, N-ethyl-, N-propyl, N-(2-hydroxyethyl)- and N-(2-methoxyethyl)-piperazines), etc.

The lower alkyl group denoted by $R^3$ is preferably a straight-chain or branched lower alkyl group of 1 to 4 carbon atoms, i.e. methyl, ethyl, propyl, isopropyl, butyl, isobutyl, sec-butyl, tert-butyl. The lower alkyl groups which may be substituted on Q, the ethylene or trimethylene group, may be alkyl groups same with those mentioned for $R^3$.

When ring A or/and ring B are substituted, the substituent(s) may be one or more, the same or different, in optional substitutable positions.

The halogen which may be substituent on rings A and B may for example be fluorine, chlorine, bromine or iodine, the alkyl which may be substituent on rings A and B may be lower alkyl groups same with those mentioned for $R^3$ and the alkoxy which may be substituent on rings A and B may be lower alkoxy groups of 1 to 4 carbon atoms just as mentioned in the definition of alkoxy which may be substituent on alkyls $R^1$ and $R^2$.

The pharmaceutically acceptable salts of the compounds (I) are acid addition salts exemplified by inorganic acid salts, such as hydrochloride, sulfate and hydrobromide, and organic acid salts such as acetate, oxalate, malonate, succinate, tartarate, maleate, furmarate and palmitate.

The benzodiazepine derivatives of the above general formula (I) and their pharmaceutically acceptable salts show a tranquilizing effect, a muscle relaxing effect, an anticonvulsive effect, a sedative effect, a sleep-inducing effect, etc., and furthermore, these compounds show low toxicity and less side effect. Taking advantage of these properties, these compounds can be safely used as tranquilizers, muscle relaxants, sedatives, anticonvulsants, sleep inducers, etc. When a compound (I) is used as such a medicine, it can be administered, either as it is or in admixture with a pharmaceutically acceptable vehicle, excipient or/and dilutent, orally or parenterally in various dosage forms such as powders, granules, tablets, capsules, suppositories and injections. While the dosage varies with the type and symptoms of disorder or ailment to be dealt with, usual oral dosage is about 0.1 mg. to about 30 mg. daily for human adults.

The object compound of this invention can be prepared by reacting a compound of the general formula (II):

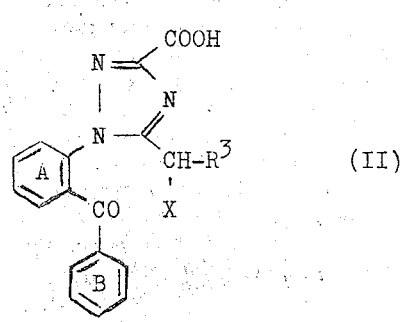

(wherein X stands for halogen atom and all other symbols and rings A and B have the respective meanings given above) or a reactive derivative at the carboxyl function thereof with a compound of the general formula (III):

(III)

(wherein R¹ and R² have the respective meanings given above) to obtain a compound of the general formula (IV):

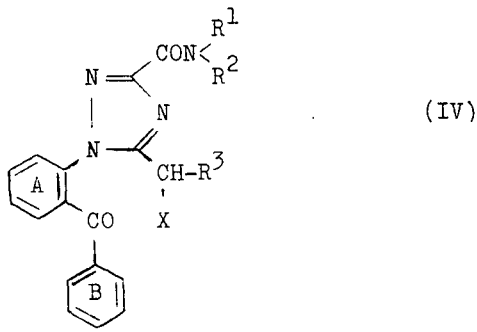
(IV)

(wherein all the symbols and rings A and B have the respective meanings given above) (step A) and, then, reacting the compound (IV) with a compound of the general formula (V):

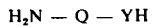 (V)

(wherein symbols Q and Y have the respective meanings given above) (step B).

The halogen represented by X includes fluorine, chlorine, bromine and iodine.

The reactive derivative at carboxyl function of compound (II), in the context of this invention, includes the esters with lower alkyls of about 1 to 4 carbon atoms (e.g. methyl, ethyl, propyl, isopropyl, butyl, isobutyl, sec-butyl, or tert-butyl), active esters (e.g. 2,4-dinitrophenyl, pentachlorophenyl, N-hydroxysuccinimido and other esters), acid halides (e.g. acid chloride, acid bromide, etc.) and mixed acid anhydrides (e.g. mixed acid anhydrides with monomethyl carbonate, monoethyl carbonate, etc.).

The above-mentioned alkyl esters can be produced by treating a compound (II) with an alcohol corresponding to the alkyl moiety of the ester in the presence of an acid catalyst (e.g. hydrochloric acid, sulfuric acid, p-toluenesulfonic acid, etc.) at a temperature ranging from room temperature to the boiling point of the alcohol used. The active esters can easily be produced by condensing a compound (II) with a phenol or a hydroxyl-containing compound corresponding to the ester residue (e.g. N-hydroxysuccinimide, 2,4-dinitrophenol, pentachlorophenol, etc.) in the presence of DCC (dicyclohexylcarbodiimide). The acid halides can easily be produced by reacting compound (II), for example with a chloride or an oxychloride of phosphorus (e.g. phosphorus trichloride, phosphorus tribromide, phosphorus pentachloride, phosphorus oxychloride, etc.) or thionyl chloride, if necessary in a suitable solvent (e.g. benzene, toluene, xylene, chloroform, dichloromethane, tetrahydrofuran) at a temperature ranging from about −10°C to about the boiling point of the solvent used. The mixed acid anhydride can easily be prepared in the routine manner, too, for example by reacting compound (II) with about one equivalent of a chlorocarbonic ester in a solvent (e.g. tetrahydrofuran, dioxane, dimethylformamide, etc.) in the presence of about one equivalent of a base (e.g. triethylamine) under cooling.

While the reactive derivative at carboxyl function of compound (II) thus produced can be isolated and purified if desired, it is also recommended in the reactions of this invention to use directly the reaction mixture as such or the residue after removing off the solvent from the reaction mixture.

The reaction in step A of this invention is performed by reacting a compound (II) or a reactive derivative at carboxyl function thereof with a compound (III). The reaction proceeds even in the absence of a solvent because one of reactants (III) may function as a solvent as well, but the reaction can proceed smoothly by employment of a solvent. While this reaction does not necessarily require a condensing agent, particularly when the free carboxylic acid of the general formula (II) as such is used as one of the reactants, the reaction is more desirably conducted in the presence of a condensing agent. The solvent to be used in the present reaction is exemplified by ethyl acetate and others as well as the solvents which are usable in the preparation of said reactive derivative at carboxyl function of compound (II), insofar the solvent will not adversely affect the reaction. The condensing agent which may be employed includes DCC (dicyclohexylcarbodiimide), carbonyldiimidazole, etc. The proportions of starting compounds in this reaction are ordinarily about 1 to 10 moles of compound (III) for every mole of compound (II) and, when a condensing agent is employed, about 1 to 1.5 mole of (III) to each mole of compound (II). In this connection, when the compound of general formula (III) is ammonia, it can be used in optional forms such as liquid ammonia, aqueous ammonia, etc. Further, the reaction may at times be accelerated and provide better results when a basic substance (e.g. triethylamine, N-methylpiperidine and other tertiary organic amines) is allowed to be present in the reaction system. The proportion of the basic substance for this purpose is generally speaking, about 1 to 3 moles to each mole of compound (II). This reaction may be carried out ordinarily under cooling to around room temperature.

The reaction in step B of this invention is performed by reacting a compound (IV) with a compound (V). The molar ratio of compound (V)/compound (IV) is ordinarily about 1/1 to 1/10. While the reaction proceeds even in the absence of a solvent, the reaction can proceed smoothly by employing a solvent. The solvent may usually be selected from among alcohols (e.g. methanol, ethanol, propanol, butanol, etc.), aliphatic and aromatic hydrocarbons and halogenated hydrocarbons (e.g. hexane, benzene, toluene, xylene, chloroform, dichloromethane, etc.), dialkylformamide (e.g. dimethyl-, diethyl- and other formamides), phenol, etc. The reaction temperature may be optionally selected from the range between room temperature and 200°C and, when a solvent is used, the reaction is generally conducted under heating at a temperature around the boiling point of the solvent. In conducting the reaction of step B, more satisfactory results are sometimes obtained when a metal iodide (e.g. potassium iodide, sodium iodide, etc.) is added to the reaction system or when compound (IV) is previously treated with an iodide. It should further be understood that where compound (III) and compound (V) are identical, the contemplated compound (I) can be produced by conducting the two steps of this invention, namely step (A) and step (B), continuously without isolating the intermediate compound (IV).

The end product compound (I) thus produced can be obtained in optional purity by separation and purification procedures known per se, such as recrystallization, chromatography, etc.

The compound of the general formula (II), one of the starting compounds in the method of this invention, can be prepared from 2-aminobenzophenone derivatives by the route shown below.

(wherein $R^4$ stands for lower alkyl group same with that mentioned for $R^3$; $X^1$ stands for halogen atom same with that mentioned for X; and all the other symbols and rings A and B are as previously defined)

Thus, 2-aminobenzophenones of formula [1] are known compounds which have already been described in the literature, for example, 2-amino-5-chlorobenzophenone [*Journal of Chemical Society* 85, 344 (1904)], 2-amino-2',5-dichlorobenzophenone [*Journal of Organic Chemistry* 26, 4488 (1961)], etc.

The compound [1] gives a diazonium salt [2] by diazotation reaction which is known per se. Then, this diazonium salt [2] is coupled with an acetoacetic acid ester, usually in the presence of an acid acceptor (e.g. sodium acetate, potassium acetate, etc.), using 1 to 1.5

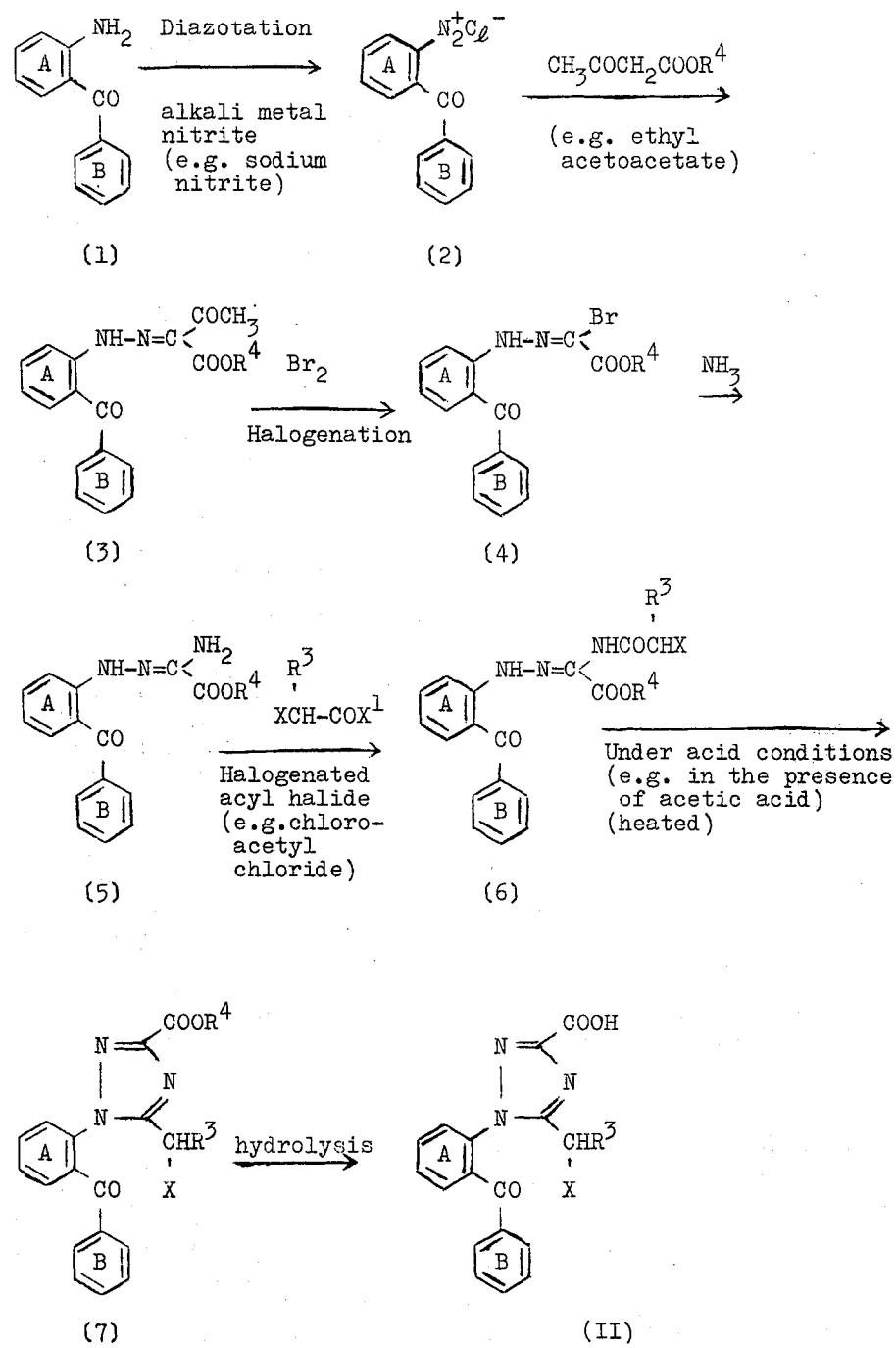

mole, preferably 1.1 to 1.3 mole of said ester to diazonium salt [2] prepared from one mole of compound [1], whereupon the corresponding (2-benzoylphenylazo)acetoacetic acid ester [3] is obtained. Then, using about 1 to 3 moles of halogen, e.g. bromine, to each mole of compound [3], the latter compound [3] is treated in a solvent inert to the halogen (e.g. acetic acid), whereupon the acetyl group is replaced selectively by the halogen to give the compound [4]. This compound is treated with ammonia to obtain compound [5] and then treated with an α-halogenated acyl halide to produce compound [6]. Compound [6], upon treatment under acidic conditions, for example, with acetic acid or monochloroacetic acid, is readily cyclized to give a triazolyl derivative [7]. Cyclization of [6] to [7] is also performed with a basic substance such as imidazole and 2-methylimidazole. Compound [7] can per se be used as a starting material in the method of this invention, but it may be converted to compound (II) by routine hydrolytic means, e.g. by treatment with alkali hydroxide. Of course, by the procedure described in this specification, compound (II) can be made into reactive derivative at carboxyl function of (II) which is also a starting material according to this invention.

Compound [5], an intermediate for the preparation of the starting compound (II), can also be prepared by the following alternate route;

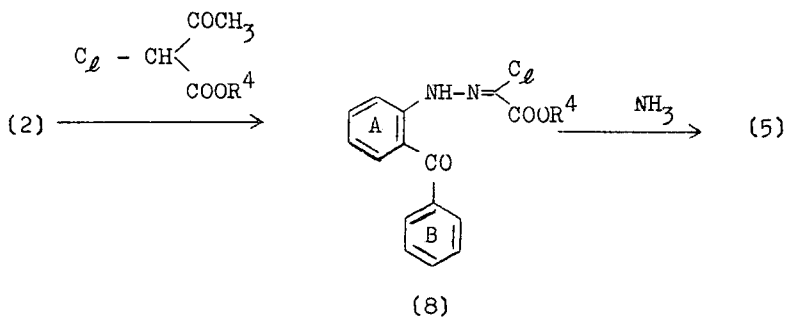

(wherein R⁴ and rings A and B are as previously defined)

Compound [8] is obtained by coupling of [2] with 2-chloroacetoacetic acid ester under conditions similar to those used in the coupling of [2] with acetoacetic acid ester which is described previously. Reaction of [8] with ammonia is also carried out in a similar manner to that used in reaction of [4] with ammonia.

In the present specification, positions of the substituents of compound (I) are designated according to the following numbering of the ring system:

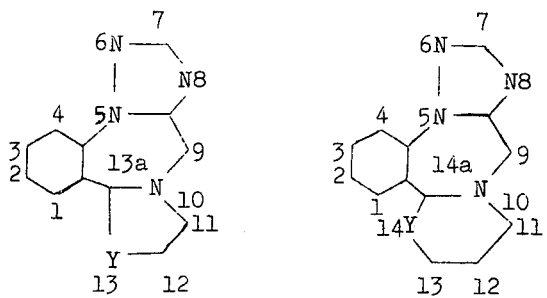

In the following examples and reference examples, "part(s)" is on the basis of weight unless otherwise stated, and the relationship between "weight part" and "volume part" is the same as between "gram" and "milliliter".

EXAMPLE 1

Under cooling with ice and stirring, to a solution of 7.5 parts of 1-(2-benzoyl-4-chlorophenyl)-5-chloromethyl-1H-1,2,4-triazole-3-carboxylic acid and 2.8 volume parts of triethylamine in 100 volume parts of dry tetrahydrofuran, 2.0 volume parts of ethyl chlorocarbonate is added dropwise. The solution is then added dropwise to 200 volume parts of ice-cooled concentrated aqueous ammonia (28 %). After stirring for 10 minutes, the mixture is diluted with water and extracted with ethyl acetate. The ethyl acetate layer is washed with water and the solvent is distilled off. The residue is treated with ether to obtain 1-(2-benzoyl-4-chlorophenyl)-5-chloromethyl-1H-1,2,4-triazole-3-carboxamide as crystals. Recrystallization from ethanol gives colorless crystals melting at 122°–124°C (this product includes ½ ethanol of crystallization).

Elemental analysis ($C_{17}H_{12}Cl_2N_4O_2 \cdot \frac{1}{2}C_2H_5OH$): Calcd. C, 54.28; H, 3,80; N, 14.07. Found C, 54.36; H, 3.78; N, 13.85.

After a manner similar to that described above, the following compounds are prepared:

1-(2-Benzoyl-4-methylphenyl)-5-chloromethyl-1H-1,2,4-triazole-3-carboxamide; melting point 157°–158°C (recrystallization from ethanol).

1-[4-Chloro-2-(2-chlorobenzoyl)phenyl]-5-chloromethyl-1H-1,2,4-triazole-3-carboxamide; melting point 165°–166°C (recrystallization from ethanol).

EXAMPLE 2

To a solution of 0.375 part of 1-(2-benzoyl-4-chlorophenyl)-5-chloromethyl-1H-1,2,4-triazole-3-carboxamide in 4 volume parts of ethanol is added 0.2 volume part of ethanolamine. The mixture is refluxed for 7 hours and, then, the solvent is distilled off. Water is added to the residue and the precipitate is collected by filtration. The procedure yields 2-chloro-13a-phenyl-11,12-dihydro-9H,13aH-oxazolo[3,2-d]-s-triazolo[1,5-a]benzodiazepine-7-carboxamide as crystals. Recrystallization from ethanol-methanol gives colorless prisms melting at 242°–243°C.

Elemental analysis ($C_{19}H_{16}ClN_5O_2$): Calcd. C, 59.76; H, 4.22; N, 18.34. Found C, 59.70; H, 4.10; N, 17.94.

After a manner similar to that described above, the following compounds are prepared:

11,12-Dihydro-2-methyl-13a-phenyl-9H,13aH-oxazolo[3,2-d]-s-triazolo[1,5-a][1,4]benzodiazepine-7-carboxamide; melting point 260°–261°C (recrystallization from methanol).
2-Chloro-13a-(2-chorophenyl)-11,12-dihydro-9H,13aH-oxazolo-[3,2-d]-s-triazolo[1,5-a][1,4]benzodiazepine-7-carboxamide; melting point 232°–233°C (recrystallization from methanol).

EXAMPLE 3

To a stirred solution of 3.76 parts of 1-(2-benzoyl-4-chlorophenyl)-5-chloromethyl-1H-1,2,4-triazole-3-carboxylic acid and 1.4 volume part of triethylamine in 60 volume parts of dry tetrahydrofuran, 1.0 volume part of ethyl chlorocarbonate is added dropwise under cooling with ice-salt. After 5 minutes, a solution of 1.2 volume part of ethanolamine in 10 volume parts of dry tetrahydrofuran is added dropwise to the mixture. After evaporation of the solvent below 40°C under reduced pressure, the residue is diluted with water. This procedure yields 1-(2-benzoyl-4-chlorophenyl)-5-chloromethyl-N-(2-hydroxyethyl)-1H-1,2,4-triazole-3-carboxamide as crystals. Recrystallization from ethanol gives colorless prisms melting at 170°–171°C.

Elemental analysis ($C_{19}H_{16}Cl_2N_4O_3$): Calcd. C, 54.43; H, 3.85; N, 13.36. Found C, 54.21; H, 3.79; N, 13.17.

EXAMPLE 4

A mixture of 0.82 part of 1-(2-benzoyl-4-chlorophenyl)-5-chloromethyl-N-(2-hydroxyethyl)-1H-1,2,4-triazole-3-carboxamide, 0.6 volume part of ethanolamine and 12 volume parts of ethanol is refluxed for 17 hours. The mixture is diluted with water and extracted with chloroform. The chloroform layer is washed with water and dried over sodium sulfate. Evaporation of the solvent followed by treatment of the residue with ethanol yields 2-chloro-11,12-dihydro-N-(2-hydroxyethyl)-13a-phenyl-9H,13aH-oxazolo[3,2-d]-s-triazolo[1,5-a][1,4]benzodiazepine-7-carboxamide as crystals. Recrystallization from ethanol-ethyl acetate gives colorless fine crystals melting at 168°–169°C.

Elemental analysis ($C_{21}H_{20}ClN_5O_3$): Calcd. C, 59.22; H, 4.73; N, 16.45. Found C, 59.29; H, 4.58; N, 16.31.

EXAMPLE 5

A mixture of 0.355 part of 1-(2-benzoyl-4-methylphenyl)-5-chloromethyl-1H-1,2,4-triazole-3-carboxamide, 0.4 volume part of isopropanolamine and 6 volume parts of ethanol is refluxed for 20 hours. After evaporation of the solvent, water is added to the residue to yield 11,12-dihydro-2,12-dimethyl-13a-phenyl-9H,13aH-oxazolo[3,2-d]-s-triazolo[1,5-a][1,4]benzodiazepine-7-carboxamide as crystals. Recrystallization from methanol gives colorless prisms melting at 245°–249°C.

EXAMPLE 6

A mixture of 0.355 part of 1-(2-benzoyl-4-methylphenyl)-5-chloromethyl-1H-1,2,4-triazole-3-carboxamide, 0.4 volume part of 3-aminopropanol and 6 volume parts of ethanol is refluxed for 63 hours, and the solvent is evaporated. To the residue water is added and the mixture is extracted with ethyl acetate. The ethyl acetate layer is washed with water and the solvent is evaporated. The residue is treated with ethanol to yield 11,12-dihydro-2-methyl-14a-phenyl-9H,13H,14aH-[1,3]oxazino[3,2-d]-s-triazolo[1,5-a]-[1,4]benzodiazepine-7-carboxamide as crystals. Recrystallization from aqueous ethanol gives colorless prisms melting at 207°–209°C.

EXAMPLE 7

After a manner similar to that described in Example 1 except the use of 60 volume parts of 40 % aqueous dimethylamine instead of 200 volume parts of concentrated aqueous ammonia, 1-(2-benzoyl-4-chlorophenyl)-5-chloromethyl-N,N-dimethyl-1H-1,2,4-triazole-3-carboxamide is obtained as crystals. Recrystallization from ethanol gives colorless prisms melting at 158°–160°C.

Elemental analysis ($C_{19}H_{16}Cl_2N_4O_2$): Calcd. C, 56.59; H, 4.00; N, 13.89. Found C, 56.46; H, 3.75; N, 13.88.

EXAMPLE 8

Under conditions similar to those described in Example 2, treatment of 1-(2-benzoyl-4-chlorophenyl)-5-chloromethyl-N,N-dimethyl-1H-1,2,4-triazole-3-carboxamide with ethanolamine gives 2-chloro-11,12-dihydro-N,N-dimethyl-13a-phenyl-9H,13aH-oxazolo[3,2-d]-s-triazolo[1,5-a][1,4]benzodiazepine-7-carboxamide as crystals. Recrystallization from ethanol yields colorless needles melting at 194°–195°C.

Elemental analysis ($C_{21}H_{20}ClN_5O_2$): Calcd. C 61.53, H 4.92, N 17.09. Found C 61.40, H 4.79, N 16.76.

EXAMPLE 9

To a stirred suspension of 5.07 parts of 1-[4-chloro-2-(4-methoxybenzoyl)phenyl]-5-chloromethyl-1H-1,2,4-triazole-3-carboxylic acid triethylammonium salt in 60 volume parts of dry tetrahydrofuran, 1.0 volume part of ethyl chlorocarbonate is added under cooling with ice-salt. After 5 minutes a solution of 2.6 volume parts of morpholine in 3 volume parts of dry tetrahydrofuran is added to the mixture. After stirring for an additional 5 minutes the reaction mixture is diluted with water and concentrated under reduced pressure. The concentrate is extracted with ethyl acetate and the ethyl acetate layer is washed with water. After evaporation of the solvent the residue is treated with ethanol-ether to yield 1-[4-chloro-2-(4-methoxybenzoyl)-phenyl]-5-chloromethyl-3-morpholinocarbonyl-1H-1,2,4-triazole as crystals. Recrystallization from aqueous ethanol gives colorless prisms melting at 180°–181°C. The crystals are hemihydrate.

Elemental analysis ($C_{22}H_{20}Cl_2N_4O_4 \cdot \frac{1}{2} H_2O$): Calcd. C, 54.55; H, 4.37; N, 11.57. Found C, 54.73; H, 4.16; N, 11.53.

EXAMPLE 10

A mixture of 0.475 part of 1-[4-chloro-2-(4-methoxybenzoyl]-phenyl)-5-chloromethyl-3-morpholinocarbonyl-1H-1,2,4-triazole (hemihydrate), 0.3 volume part of ethanolamine and 6 volume parts of ethanol is refluxed for 17 hours. After dilution with water the mixture is extracted with ethyl acetate. The ethyl acetate layer is washed with water and dried over sodium sulfate. The solvent is evaporated and the residue treated with ethanol-ether to give 4-{2-chloro-11,12-dihydro-13a-(4-methoxyphenyl)-9H,13aH-oxazolo[3,2-d]-s-triazolo[1,5-a][1,4]benzodiazepin-7-yl} carbonylmorpholine as crystals. Recrystallization from ethanol gives colorless needles melting at 134°–135°C.

Elemental analysis ($C_{24}H_{24}ClN_5O_4$): Calcd. C, 59.81; H, 5.02; N, 14.53. Found C, 59.48; H, 4.92; N, 14.38.

EXAMPLE 11

To a stirred solution of 3.41 parts of 1-(2-benzoyl-phenyl)-5-chloromethyl-1H-1,2,4-triazole-3-carboxylic acid and 1.4 volume part of triethylamine in 60 volume parts of dry tetrahydrofuran, 1.0 volume part of ethyl chlorocarbonate is added dropwise under cooling with ice-salt. After 10 minutes, a solution of 2.0 parts of N-methylpiperazine in 10 volume parts of dry tetrahydrofuran is added dropwise to the mixture. After stirring for an additional 10 minutes the reaction mixture is diluted with water and extracted with ethyl acetate. The ethyl acetate layer is washed with water. Evaporation of the solvent yields crude 1-(2-benzoylphenyl)-5-chloromethyl-3-(4-methyl-piperazinyl)carbonyl-1H-1,2,4-triazole. To this is then added 60 volume parts of ethanol and 3 volume parts of ethanolamine, and the mixture is refluxed for 17 hours. The reaction mixture is diluted with water and extracted with ethyl acetate. The ethyl acetate layer is washed with water and evaporated to remove the solvent. The residue is treated with ethanol-ether to yield 1-{11,12-dihydro-13a-phenyl-9H,13aH-oxazolo[3,2-d]-s-triazolo[1,5-a][1,4] benzodiazepine-7-yl } carbonyl-4 -methylpiperazine as crystals. Recrystallization from acetone gives colorless needles melting at 190°–191°C.

Elemental analysis ($C_{24}H_{26}N_6O_2$): Calcd. C, 66.95; H, 6.09; N, 19.52. Found C, 66.85; H, 6.05; N, 19.34.

After a similar manner to the above, the following compounds can be prepared.

1. 2-Chloro-11,12-dihydro-N-methyl-13a-phenyl-9H,13aH-oxazolo-[3,2-d]-s-triazolo[1,5-a][1,4]benzodiazepine-7-carboxamide,
2. 2-Chloro-11,12-dihydro-N,N-dimethyl-13a-phenyl-9H,13aH-oxazolo[3,2-d]-s-triazolo[1,5-a][1,4]benzodiazepine-7-carboxamide,
3. 2-Chloro-N,N-diethyl-11,12-dihydro-13a-phenyl-9H,13aH-oxazolo-[3,2-d]-s-triazolo[1,5-a][1,4]benzodiazepine-7-carboxamide,
4. 2-Chloro-N-ethyl-11,12-dihydro-N-methyl-13a-phenyl-9H,13aH-oxazolo[3,2-d]-s-triazolo[1,5-a][1,4]benzodiazepine-7-carboxamide,
5. 2-Chloro-N-ethyl-11,12-dihydro-13a-phenyl-N-propyl-9H,13aH-oxazolo[3,2-d]-s-triazolo[1,5-a][1,4]benzodiazepine-7-carboxamide,
6. 1-[(2-Chloro-11,12-dihydro-13a-phenyl-9H,13aH-oxazolo[3,2-d]-s-triazolo[1,5-a][1,4]benzodiazepin-7-yl)carbonyl]pyrrolidine,
7. 1-[(2-Chloro-11,12-dihydro-13a-phenyl-9H,13aH-oxazolo[3,2-d]-s-triazolo[1,5-a][1,4]benzodiazepin-7-yl)carbonyl]piperidine,
8. 4-[(2-Chloro-11,12-dihydro-13a-phenyl-9H,13aH-oxazolo[3,2-d]-s-triazolo[1,5-a][1,4]benzodiazepin-7-yl)carbonyl]morpholine,
9. 1-[(2-Chloro-11,12-dihydro-13a-phenyl-9H,13aH-oxazolo[3,2-d]-s-triazolo[1,5-a][1,4]benzodiazepin-7-yl)carbonyl]-4-methylpiperazine,
10. 1-[(2-Chloro-11,12-dihydro-13a-phenyl-9H,13aH-oxazolo[3,2-d]-s-triazolo[1,5-a][1,4]benzodiazepin-7-yl)carbonyl]-4-ethylpiperazine,
11. 1-[(2-Chloro-11,12-dihydro-13a-phenyl-9H,13aH-oxazolo[3,2-d]-s-triazolo[1,5-a][1,4]benzodiazepin-7-yl)carbonyl]-4-(2-hydroxyethyl)piperazine,
12. 1-[(2-Chloro-11,12-dihydro-13a-phenyl-9H,13aH-oxazolo[3,2-d]-s-triazolo[1,5-a][1,4]benzodiazepin-7-yl)carbonyl]-4-(2-methoxyethyl)piperazine,
13. 2-Chloro-11,12-dihydro-11-methyl-13a-phenyl-9H,13aH-oxazolo-[3,2-d]-s-triazolo[1,5-a][1,4]benzodiazepine-7-carboxamide,
14. 2-Chloro-11,12-dihydro-12-methyl-13a-phenyl-9H,13aH-oxazolo-[3,2-d]-s-triazolo[1,5-a][1,4]benzodiazepine-7-carboxamide,
15. 2-Chloro-N,N-diethyl-11,12-dihydro-12-methyl-13a-phenyl-9H,13aH-oxazolo[3,2-d]-s-triazolo[1,5-a][1,4]benzodiazepine-7-carboxamide,
16. 2-Chloro-11,12-dihydro-14a-phenyl-9H,13H,14aH[1,3]oxazino-[3,2-d]-s-triazolo[1,5-a][1,4]benzodiazepine-7-carboxamide,
17. 2-Chloro-11,12-dihydro-13a-phenyl-9H,13aH-imidazo[1,2-d]-s-triazolo[1,5-a][1,4]benzodiazepine-7-carboxamide,
18. 2-Chloro-N,N-diethyl-11,12-dihydro-13a-phenyl-9H,13aH-imidazo[1,2-d]-s-triazolo[1,5-a][1,4]benzodiazepine-7-carboxamide,
19. 2-Chloro-11,12-dihydro-13a-phenyl-9H,13aH-thiazolo[3,2-d]-s-triazolo[1,5-a][1,4]benzodiazepine-7-carboxamide,
20. 2-Chloro-1,1,12-dihydro-9-methyl-13a-phenyl-9H,13aH-oxazolo-[3,2-d]-s-triazolo[1,5-a][1,4]benzodiazepine-7-carboxamide,
21. 2-Chloro-13a-(2-chlorophenyl)-11,12-dihydro-N-methyl-9H,13aH-oxazolo[3,2-d]-s-triazolo[1,5-a][1,4]benzodiazepine-7-carboxamide,
22. 2-Chloro-13a-(2-chlorophenyl)-11,12-dihydro-N,N-dimethyl-9H,13aH-oxazolo[3,2-d]-s-triazolo[1,5-a][1,4]benzodiazepine-7-carboxamide,
23. 2-Chloro-13a-(2-chlorophenyl)-N,N-diethyl-11,12-dihydro-9H,13aH-oxazolo[3,2-d]-s-triazolo[1,5-a][1,4]benzodiazepine-7-carboxamide,
24. 4-[(2-Chloro-13a-(2-chlorophenyl)-11,12-dihydro-9H,13aH-oxazolo[3,2-d]-s-triazolo[1,5-a][1,4]benzodiazepin-7-yl)carbonyl]-morpholine,
25. 2-Chloro-13a-(2-chlorophenyl)-11,12-dihydro-12-methyl-9H,13aH-oxazolo[3,2-d]-s-triazolo[1,5-a][1,4]benzodiazepine-7-carboxamide,
26. 2-Chloro-14a-(2-chlorophenyl)-11,12-dihydro-9H,13H,14aH-[1,3]oxazino[3,2-d]-s-triazolo[1,5-a][1,4]benzodiazepine-7-carboxamide,
27. 2-Chloro-11,12-dihydro-13a-(2-fluorophenyl)-9H,13aH-oxazolo[3,2-d]-s-triazolo[1,5-a][1,4]benzodiazepine-7-carboxamide,
28. 2-Chloro-13a-(2,6-difluorophenyl)-11,12-dihydro-9H,13aH-oxazolo[3,2-d]-s-triazolo[1,5-a][1,4]benzodiazepine-7-carboxamide,
29. 2-Chloro-N,N-diethyl-13a-(2,6-difluorophenyl)-11,12-dihydro-12-methyl-9H,13aH-oxazolo[3,2-d]-s-triazolo[1,5-a][1,4]benzodiazepine-7-carboxamide,
30. 2-Chloro-11,12-dihydro-13a-(4-methoxyphenyl)-9H,13aH-oxazolo-[3,2-d]-s-triazolo[1,5-a][1,4]benzodiazepine-7-carboxamide,
31. 2-Chloro-11,12-dihydro-13a-(4-methoxyphenyl)-12-methyl-9H,13aH-oxazolo[3,2-d]-s-triazolo[1,5-a][1,4]benzodiazepine-7-carboxamide,
32. 11,12-Dihydro-13a-phenyl-9H,13aH-oxazolo[3,2-d]-s-triazolo-[1,5-a][1,4]benzodiazepine-7-carboxamide, 33. 13a-(2-Chlorophenyl)-11,12-dihydro-9H,13aH-oxazolo[3,2-d]-s-triazolo[1,5-a][1,4]benzodiazepine-7-carboxamide,
34. 13a-(2-Chlorophenyl)-N,N-diethyl-11,12-dihydro-12-methyl-9H,13aH- oxazolo [3,2-d]-s-triazolo[1,5-a][1,4]benzodiazepine-7-carboxamide,
35. 11,12-Dihydro-2-nitro-13a-phenyl-9H,13aH-oxazolo[3,2-d]-s-triazolo[1,5-a][1,4]benzodiazepine-7-carboxamide,
36. 11,12-Dihydro-2-methoxy-13a-phenyl-9H,13aH-oxazolo[3,2-d]-s-triazolo[1,5-a][1,4]benzodiazepine-7-carboxamide,
37. 11,12-Dihydro-2,3-dimethoxy-13a-phenyl-9H,13aH-oxazolo[3,2-d]-s-triazolo[1,5-a][1,4]benzodiazepine-7-carboxamide,
38. 11,12-Dihydro-13a-phenyl-2-trifluoromethyl-9H,13aH-oxazolo-[3,2-d]-s-triazolo[1,5-a][1,4]benzodiazepine-7-carboxamide, and
39. N,N-Diethyl-11,12-dihydro-12-methyl-13a-phenyl-2-trifluoromethyl-9H,13aH-oxazolo[3,2-d]-s-triazolo[1,5-a][1,4]benzodiazepine-7-carboxamide.

REFERENCE EXAMPLE 1

To a stirred solution of 11.5 parts of 2-amino-5-chlorobenzophenone in 50 volume parts of acetic acid and 15 volume parts of concentrated hydrochloric acid, a solution of 3.5 parts of sodium nitrite in 20 volume parts of water is added dropwise under cooling with ice for about 30 minutes. To the mixture is added a solution of 13.5 parts of zinc chloride in 60 volume parts of water and the precipitated diazonium salt is collected by filtration.

The diazonium salt is then added to a stirred solution of 7.8 parts of ethyl acetoacetate and 20 parts of potassium acetate in 200 volume parts of 50 % ethanol. After stirring the mixture for 1 hour, the precipitate which separated is collected by filtration, washed with water and ethanol, and dried. The procedure gives ethyl (2-benzoyl-4-chlorophenylazo)acetoacetate as crystals. Recrystallization from ethanol yields yellow needles melting at 132°–133°C.

Elemental analysis (C$_{19}$H$_{17}$ClN$_4$O$_4$): Calcd. C, 61.21; H, 4.00; N, 7.52. Found C, 61.26; H, 4.17; N, 7.29.

After a manner similar to that described above, the following compounds are prepared:
Ethyl (2-benzoyl-4-methylphenylazo)acetoacetate; melting point 130°–131°C (recrystallization from ethanol);
Ethyl [4-chloro-2-(2-chlorobenzoyl)phenylazo]acetoacetate; melting point 144°–145°C (recrystallization from ethanol);
Ethyl [4-chloro-2-(4-methoxybenzoyl)phenylazo]acetoacetate; melting point 144°–145°C (recrystallization from ethanol);

REFERENCE EXAMPLE 2

To a solution of 3.7 parts of ethyl (2-benzoyl-4-chlorophenylazo)acetoacetate in 100 volume parts of acetic acid are added 4.1 parts of sodium acetate and 1.5 volume part of bromine. The mixture is stirred at room temperature overnight and the acetic acid is distilled off under reduced pressure. The residue is diluted with ice-water and extracted with ethyl acetate. The ethyl acetate layer is washed with water and dried over sodium sulfate. The solvent is distilled off and the residue is treated with ethanol, whereupon ethyl (2-benzoyl-4-chlorophenylazo)-bromoacetate is obtained as yellow crystals. Recrystallization from ether yields yellow needles melting at 138°–139°C.

Elemental analysis (C$_{17}$H$_{14}$BrClN$_2$O$_3$): Calcd. C, 49.84; H, 3.44; N, 6.84. Found C, 49.62; H, 3.25; N, 6.81.

After a manner similar to that described above, the following compounds are prepared:
Ethyl (2-benzoyl-4-methylphenylazo)bromoacetate; melting point 109°–110°C (recrystallization from ethanol);
Ethyl [4-chloro-2-(2-chlorobenzoyl)phenylazo]-bromoacetate; melting point 144°–145°C (recrystallization from ethanol);
Ethyl [4-chloro-2-(4-methoxybenzoyl)phenylazo]-bromoacetate; melting point 138°–139°C (recrystallization from chloroform-ethanol).

REFERENCE EXAMPLE 3

To a solution of 8.1 parts of ethyl (2-benzoyl-4-chlorophenylazo)bromoacetate in 16 volume parts of ether is added 160 volume parts of concentrated aqueous ammonia. After stirring the mixture for 1 hour at room temperature, the ether layer is separated, washed with water and evaporated to remove the solvent. The crystalline residue is collected by filtration, washed with ethanol and dried. The procedure gives ethyl (2-benzoyl-4-chlorophenylazo)-aminoacetate. Recrystallization from ethanol gives yellowish orange needles melting at 126°–127°C.

Elemental analysis (C$_{17}$H$_{16}$ClN$_3$O$_3$): Calcd. C, 59.05; H, 4.66; N, 12.15. Found C, 59.25; H, 4.73; N, 11.89.

After a manner similar to that described above, the following compounds are prepared:
Ethyl (2-benzoyl-4-methylphenylazo)aminoacetate; melting point 135°–136°C (recrystallization from ethanol).
Ethyl [4-chloro-2-(2-chlorobenzoyl)phenylazo]aminoacetate; oil (this material is used in the next reaction step).
Ethyl [4-chloro-2-(4-methoxybenzoyl)-phenylazo]aminoacetate; melting point 174°–176°C (recrystallization from ethanol).

REFERENCE EXAMPLE 4

To a stirred mixture of 3.4 parts of ethyl (2-benzoyl-4-chlorophenylazo)aminoacetate, 2.8 parts of potassium carbonate and 100 volume parts of benzene is added 1.5 volume part of chloroacetyl chloride dropwise. The mixture is stirred for 2 hours and, then, heated under reflux for 30 minutes. After cooling, the mixture is shaken with water and the benzene layer is separated, washed with water and dried over sodium sulfate. The solvent is then distilled off and the crystalline residue is collected by filtration, washed with water and dried. The procedure yields ethyl (2-benzoyl-4-chlorophenylazo)chloroacetylaminoacetate. Recrystallization from methanol gives yellow needles melting at 179°–180°C.

Elemental analysis (C$_{19}$H$_{17}$Cl$_2$N$_3$O$_4$): Calcd. C, 54.04; H, 4.06; N, 9.95. Found C, 54.06; H, 4.21; N, 10.26.

After a manner similar to that described above, the following compounds are prepared:
Ethyl (2-benzoyl-4-methylphenylazo)-chloroacetylaminoacetate; melting point 172°–175°C (recrystallization from ethanol).

Ethyl [4-chloro-2-(2-chlorobenzoyl)phenylazo]-chloroacetylaminoacetate; melting point 196°–198°C (recrystallization from ethyl acetate)

Ethyl [4-chloro-2-(4-methoxybenzoyl)phenylazo]-chloroacetylaminoacetate; melting point 124°–126°C (recrystallization from ethanol)

REFERENCE EXAMPLE 5

A solution of 1.5 part of ethyl (2-benzoyl-4-chlorophenylazo)-chloroacetylaminoacetate in 30 volume parts of acetic acid is refluxed for 10 minutes, and then the acetic acid is distilled off under reduced pressure. The residue is neutralized with a saturated aqueous solution of sodium bicarbonate and, then, extracted with ethyl acetate. The ethyl acetate layer is washed with water and dried over sodium sulfate. After evaporation of the solvent, the residue is treated with n-hexane to obtain ethyl 1-(2-benzoyl-4-chlorophenyl)-5-chloromethyl-1H-1,2,4-triazole-3-carboxylate as crystals.

Recrystallized from ethanol gives colorless needles melting at 119°–120°C.

Elemental analysis ($C_{19}H_{15}Cl_2N_3O_3$): Calcd. C, 56.45; H, 3.74; N, 10.40. Found C, 56.59; H, 3.40; N, 10.35.

After a manner similar to that described above the following compounds are prepared:

Ethyl 1-(2-benzoyl-4-methylphenyl)-5-chloromethyl-1H-1,2,4-triazole-3-carboxylate; melting point 97°–98°C (recrystallization from ethanol);

Ethyl 1-[4-chloro-2-(2-chlorobenzoyl)phenyl]-5-chloromethyl-1H-1,2,4-triazole-3-carboxylate; melting point 114°–115°C (recrystallization from ethanol);

Ethyl 1-[4-chloro-2-(4-methoxybenzoyl)phenyl]-5-chloromethyl-1H-1,2,4-triazole-3-carboxylate; oil (this material is used in the next reaction step)

REFERENCE EXAMPLE 6

To a solution of 6.0 parts of ethyl 1-(2-benzoyl-4-chlorophenyl)-5-chloromethyl-1H-1,2,4-triazole-3-carboxylate in 70 volume parts of methanol is added 16.5 volume parts of 1N sodium hydroxide dropwise. The hydrolysis is completed after about 15 minutes. Then, acetic acid is added to the reaction mixture to make acidic and the solvent is distilled off under reduced pressure. To the residue is added water and the precipitate is collected by filtration. The procedure gives 1-(2-benzoyl-4-chlorophenyl)-5-chloromethyl-1H-1,2,4-triazole-3-carboxylic acid as crystals. Recrystallization from ether gives colorless prisms melting at 176°–177°C.

Elemental analysis ($C_{17}H_{11}Cl_2N_3O_3$): Calcd. C, 54.27; H, 20.95; N, 11.17. Found C, 54.61; H, 2.84; N, 11.16.

After a manner similar to that described above, the following compounds are prepared:

1-(2-benzoyl-4-methylphenyl)-5-chloromethyl-1H-1,2,4-triazole-3-carboxylic acid; melting point 164°–165°C (recrystallization from ethanol-n-hexane);

1-[4-chloro-2-(2-chlorobenzoyl)phenyl]-5-chloromethyl-1H-1,2,4-triazole-3-carboxylic acid; (ethanol solvate) melting point 89°–91°C (recrystallization from ethanol);

1-[4-chloro-2-(4-methoxybenzoyl)-phenyl]-5-chloromethyl-1H-1,2,4-triazole-3-carboxylic acid; triethylammonium salt melting point 139°–140°C (recrystallization from acetone-ethyl acetate).

REFERENCE EXAMPLE 7

To a mixture of 15.0 parts of 2-aminobenzophenone, 45 volume parts of acetic acid and 2 volume parts of concentrated hydrochloric acid, a solution of 5.6 parts of sodium nitrite in 16 volume parts of water is added dropwise under ice-cooling and stirring. The mixture is then added dropwise to a solution of 15.0 parts of ethyl β-chloroacetoacetate and 20 parts of potassium acetate in a mixture of 160 volume parts of ethanol and 35 volume parts of water. After 15 minutes precipitated crystals are collected to yield ethyl (2-benzoylphenyl)azochloroacetate as crystals. Recrystallization from ethanol gives yellow needles melting at 119°–120°C.

REFERENCE EXAMPLE 8

Treatment of ethyl (2-benzoylphenyl)azochloroacetate with concentrated aqueous ammonia in ethyl acetate gives ethyl (2-benzoylphenyl)azoaminoacetate as an oil. Then the oil is chloroacetylated with chloroacetyl chloride in benzene to give ethyl (2-benzoylphenyl)azochloroacetylaminoacetate as crystals. Recrystallization from acetone gives yellow needles melting at 164°–166°C.

Cyclization of ethyl (2-benzoylphenyl)azochloroacetylaminoacetate in boiling acetic acid gives ethyl 1-(2-benzoylphenyl)-3-chloromethyl-1H-1,2,4-triazole-3-carboxylate as crystals. Recrystallization from ethanol gives colorless prisms melting at 123°–124°C.

Hydrolysis of ethyl 1-(2-benzoylphenyl)-3-chloromethyl-1H-1,2,4-triazole-3-carboxylate gives 1-(2-benzoylphenyl)-3-chloromethyl-1H-1,2,4-triazole-3-carboxylic acid as crystals melting at 90°–93°C.

What is claimed is:

1. A compound of the formula:

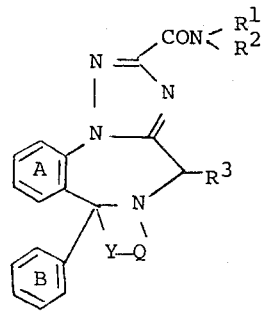

wherein $R^1$ and $R^2$ are the same or different and each stands for hydrogen or $C_1$ to $C_6$ alkyl which is unsubstituted or is substituted by hydroxy; or $R^1$ and $R^2$ when taken together with the adjacent nitrogen atom, form a morpholino or N-methylpiperazino ring; $R^3$ stands for hydrogen; Q stands for ethylene or trimethylene which is unsubstituted or is substituted by $C_1$ to $C_4$ alkyl; Y stands for —O—; and rings A and B are unsubstituted or substituted by halo, nitro, $C_1$ to $C_4$ alkyl, trifluoromethyl or $C_1$ to $C_4$ alkoxy or a pharmaceutically acceptable salt thereof.

2. A compound claimed in claim 1, wherein Q is ethylene.

3. A compound claimed in claim 1, wherein Q is trimethylene.

4. A compound claimed in claim 1, wherein Q is

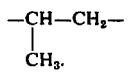

5. A compound claimed in claim 1, wherein the compound is 11,12-dihydro-2-methyl-13a-phenyl-9H,13aH-oxazolo[3,2-d]-s-triazolo[1,5-a][1,4]benzodiazepine-7-carboxamide.

6. A compound claimed in claim 1, wherein the compound is 2-chloro-13a-(2-chlorophenyl)-11,12-dihydro-9H,13aH-oxazolo[3,2-d]-s-triazolo[1,5-a][1,4]benzodiazepine-7-carboxamide.

7. A compound claimed in claim 1, wherein the compound is 2-chloro-11,12-dihydro-N-(2-hydroxyethyl)-13a-phenyl-9H,13aH-oxazolo-[3,2-d]-s-triazolo[1,5-a][1,4]benzodiazepine-7-carboxamide.

8. A compound claimed in claim 1, wherein the compound is 11,12-dihydro-2,12-dimethyl-13a-phenyl-9H,13aH-oxazolo[3,2-d]-s-triazolo-[1,5-a][1,4]benzodiazepine-7-carboxamide.

9. A compound claimed in claim 1, wherein the compound is 11,12-dihydro-2-methyl-14a-phenyl-9H,13H,14aH-[1,3]oxazino[3,2-d]-s-triazolo[1,5-a][1,4]benzodiazepine-7-carboxamide.

10. A compound claimed in claim 1, wherein the compound is 4-{2-chloro-11,12-dihydro-13a-(4-methoxyphenyl)-9H,13aH-oxazolo[3,2-d]-s-triazolo[1,5-a][1,4]benzodiazepin-7-yl}carbonylmorpholine.

11. A compound claimed in claim 1, wherein the compound is 1-{11,12-dihydro-13a-phenyl-9H,13aH-oxazolo[3,2-d]-s-triazolo[1,5-a][1,4]-benzodiazepin-7-yl}carbonyl-4-methylpiperazine.

12. A compound claimed in claim 1, wherein the compound is 2-chloro-13a-phenyl-11,12-dihydro-9H,13aH-oxazolo[3,2-d]-s-triazolo-[1,5-a][1,4]benzodiazepine-7-carboxamide.

13. A compound claimed in claim 1, wherein the compound is 2-chloro-11,12-dihydro-N,N-dimethyl-13a-phenyl-9H,13aH-oxazolo[3,2-d]-s-triazolo[1,5-a][1,4]benzodiazepine-7-carboxamide.

* * * * *